(12) United States Patent
Baust

(10) Patent No.: US 12,070,526 B2
(45) Date of Patent: Aug. 27, 2024

(54) CRYOGENIC DISINFECTION SYSTEM AND METHOD

(71) Applicant: CPSI HOLDINGS LLC, Owego, NY (US)

(72) Inventor: John M. Baust, Candor, NY (US)

(73) Assignee: CPSI Holdings LLC, Owego, NY (US)

( * ) Notice: Subject to any disclaimer, the term of this patent is extended or adjusted under 35 U.S.C. 154(b) by 631 days.

(21) Appl. No.: 17/320,637

(22) Filed: May 14, 2021

(65) Prior Publication Data

US 2021/0353803 A1  Nov. 18, 2021

Related U.S. Application Data

(60) Provisional application No. 63/024,856, filed on May 14, 2020.

(51) Int. Cl.
*A61L 2/22* (2006.01)
*A61L 2/28* (2006.01)

(52) U.S. Cl.
CPC ............... *A61L 2/22* (2013.01); *A61L 2/28* (2013.01); *A61L 2202/11* (2013.01); *A61L 2202/121* (2013.01); *A61L 2202/122* (2013.01); *A61L 2202/15* (2013.01); *A61L 2202/26* (2013.01)

(58) Field of Classification Search
CPC .......... A61L 2/22; A61L 2/28; A61L 2202/11; A61L 2202/121; A61L 2202/122; A61L 2202/15; A61L 2202/26
See application file for complete search history.

(56) References Cited

U.S. PATENT DOCUMENTS

| | | |
|---|---|---|
| 8,784,409 B2 | 7/2014 | Robilotto et al. |
| 9,408,654 B2 | 8/2016 | Baust et al. |
| 9,974,592 B2 | 5/2018 | Baust et al. |
| 10,054,262 B2 | 8/2018 | Baust et al. |
| 2017/0172791 A1 | 6/2017 | Baust et al. |
| 2018/0340654 A1 | 11/2018 | Baust et al. |

*Primary Examiner* — Sean E Conley
(74) *Attorney, Agent, or Firm* — Hoffman Warnick LLC

(57) ABSTRACT

A method of disinfecting an object using cryogenic temperatures, and a cryogenic disinfection device and cryogenic disinfection tunnel for use in such a method are disclosed herein. In various embodiments, one or more chambers are provided, capable of providing an ultralow temperature therein. An object is placed or moved to within the chamber and subjected to ultralow, e.g., cryogenic, temperatures therein for a period of time sufficient to disinfect the object to a desired depth.

19 Claims, 2 Drawing Sheets

CRYOGENIC DISINFECTION SYSTEM AND METHOD

CROSS REFERENCE TO RELATED APPLICATIONS

This patent application claims the benefit of U.S. Provisional Patent Application Ser. No. 63/024,856, filed May 14, 2020, which is incorporated by reference in its entirety as though it were fully set forth herein.

BACKGROUND OF THE INVENTION

The invention relates generally to a rapid surface disinfection or sterilization process. More particularly, the invention relates to a cryogenic disinfection system and process.

Severe acute respiratory syndrome coronavirus 2 (SARS-CoV2) is a novel coronavirus that causes coronavirus disease (COVID-19 disease), a highly infectious respiratory illness. COVID-19 was declared a pandemic by the World Health Organization on Mar. 11, 2020, and carries a mortality rate that may exceed 1%. Human to human transmission of the virus is understood to occur via droplets or contact. Current clinical management includes supportive care, including supplemental oxygen and mechanical ventilatory support when indicated, and infection prevention and control measures including containment, disinfection, sterilization, and decontamination to limit the spread of the virus.

In addition to direct or droplet contact with carriers of SARS-Cov2, COVID-19 and other infectious diseases may be spread through contact with objects that are contaminated with viral particles. Other viral and bacterial infections may be spread in a similar manner. To limit the spread, disinfection methods have been deployed including, e.g., hydrogen peroxide vapor/spray treatments, ultraviolet light, chlorine wipes and sprays, and heat treatment, e.g., autoclaving. These methods have been used, e.g., in hospitals, and on articles such as clothing and fabrics, masks, medical instruments, etc.

Mail and package delivery, a mainstay of e-commerce-driven modern life, provides additional opportunities for the spread of infectious disease through contact with contaminated objects. Envelopes and packages may be contaminated at any point in the supply and delivery chain, and may continue to carry viral and bacterial contamination for time periods varying with the strain and positioning of the microbial agent. For example, a study published in the New England Journal of Medicine demonstrated that SARS-CoV-2 can remain viable for hours to days on various surfaces including up to 24 hours on cardboard and 2-3 days on plastic and stainless steel.

Numerous practical obstacles prevent the scaling up of disinfection strategies employed in, e.g., hospital settings, for use in shipping. For example, hydrogen peroxide gas treatment is toxic and requires many minutes to hours of exposure to achieve effective decontamination. Alcohol-based sprays require object wetting and can damage shipping labels to the point of illegibility. Similar issues are associated with heat based approaches and with chlorine gas or wipe cleaning. Ultraviolet light exposure also requires extended periods of exposure, which is incompatible with current shipping timeframe demands.

A global processing or treatment system is needed that is capable of destroying all surface and embedded viral and bacterial vectors, without materially slowing the distribution process, adding secondary agents to the letters/packages, damaging letters/packages or their contents, or adding significant expense.

BRIEF DESCRIPTION OF THE INVENTION

According to a first aspect of the disclosure, a cryogenic disinfection device is provided, comprising a cryogenic disinfection chamber into which an object may be placed. The cryogenic disinfection chamber includes a manifold disposed within the cryogenic disinfection chamber, the manifold being supplied with liquid phase, gas phase, pressurized liquid, mixed gas and liquid phase, critical or supercritical cryogen used to lower the temperature within the chamber to, e.g., less than $-40°$ C., less than $-80°$ C., less than $-100°$ C., or less than $-140°$ C.

According to a second aspect of the disclosure, a cryogenic disinfection tunnel is provided for disinfecting an object. The cryogenic disinfection tunnel comprises the cryogenic disinfection device of the first aspect, in combination with other elements as described herein. The combination results in a tunnel having one or more chambers capable of providing an ultralow temperature within the chamber; and a conveyor belt for carrying the object through the one or more chambers. In use, exposure of an object to the ultralow temperatures inside the one or more chambers has the effect of disinfecting at least an outer surface of the object.

According to a third aspect of the disclosure, a method is provided for disinfecting an object. The method includes the steps of placing the object in a chamber having an ultralow interior temperature, and exposing the object to the ultralow temperature for a duration of time sufficient to destroy a virus, a bacterium, a fungus, or other microbe on a surface or embedded within the object. This method provides nontoxic disinfection of an object, including, e.g., destruction of viral particles on the object's surface.

These and other aspects, advantages and salient features of the invention will become apparent from the following detailed description, which, when taken in conjunction with the annexed drawings, disclose embodiments of the invention. In the drawings, like parts are designated by like reference characters throughout the drawings.

It is noted that the drawings of the disclosure are not necessarily to scale. The drawings are intended to depict only typical aspects of the disclosure, and therefore should not be considered as limiting the scope of the disclosure.

DETAILED DESCRIPTION OF THE INVENTION

A broad array of biologics including viruses, prokaryotic cells (e.g., bacteria, archaea, etc.), and eukaryotic cells (e.g., animal plant, insect, fungus, etc.) are susceptible to injury induced by exposure to ultralow temperatures. As used herein, "ultralow" temperatures refer to cryogenic temperatures, e.g., less than −40° C., less than −80° C., less than −100° C., or less than −140° C. Various embodiments of the present invention provide a method and devices for use in cryogenic disinfection. In particular, cryogenic temperatures are used to provide a non-toxic rapid decontamination and/or sterilization procedure for objects of all kinds, by exposing the objects to cryogenic temperatures of, e.g., less than −40° C., less than −80° C., less than −100° C., or less than −140° C. Such disinfection processes are useful in the destruction of viruses, bacteria, fungi, and other biologics inadvertently transferred by human contact, and in combatting bioterrorism events.

Certain embodiments of the present invention are described herein in the context of their use in disinfecting envelopes, packages, and other parcels sorted, processed, and delivered by mail, express mail, and logistics entities, e.g., US Postal Service (USPS), United Parcel Service (UPS), Federal Express (FedEx), DHL International GmbH (DHL), and others worldwide. In such embodiments, rapid or flash exposure of the package to cryogenic temperatures has the effect of killing viruses and bacteria on the object's surface without penetrating through the package to reach the contents, thereby avoiding damage to contents. In such embodiments, disinfection devices similar to those described herein may be deployed much like inline weighing scales, and integrated into conveyor-based handling systems to passively disinfect the surface of a package without harming the integrity of the package box, label, or contents.

Other embodiments are described in reference to their application in business, military, government, customs, port of entry, consumer or retail settings, or hospital settings for the disinfection of various items, e.g., gowns, masks, personal protective equipment (PPE), instruments, and other goods and items. Additionally, devices according to embodiments described herein may be used to support a disinfection service model in a centralized facility. However, it should be apparent to those skilled in the art that the present invention is likewise applicable to a variety of other settings.

Figure 1:
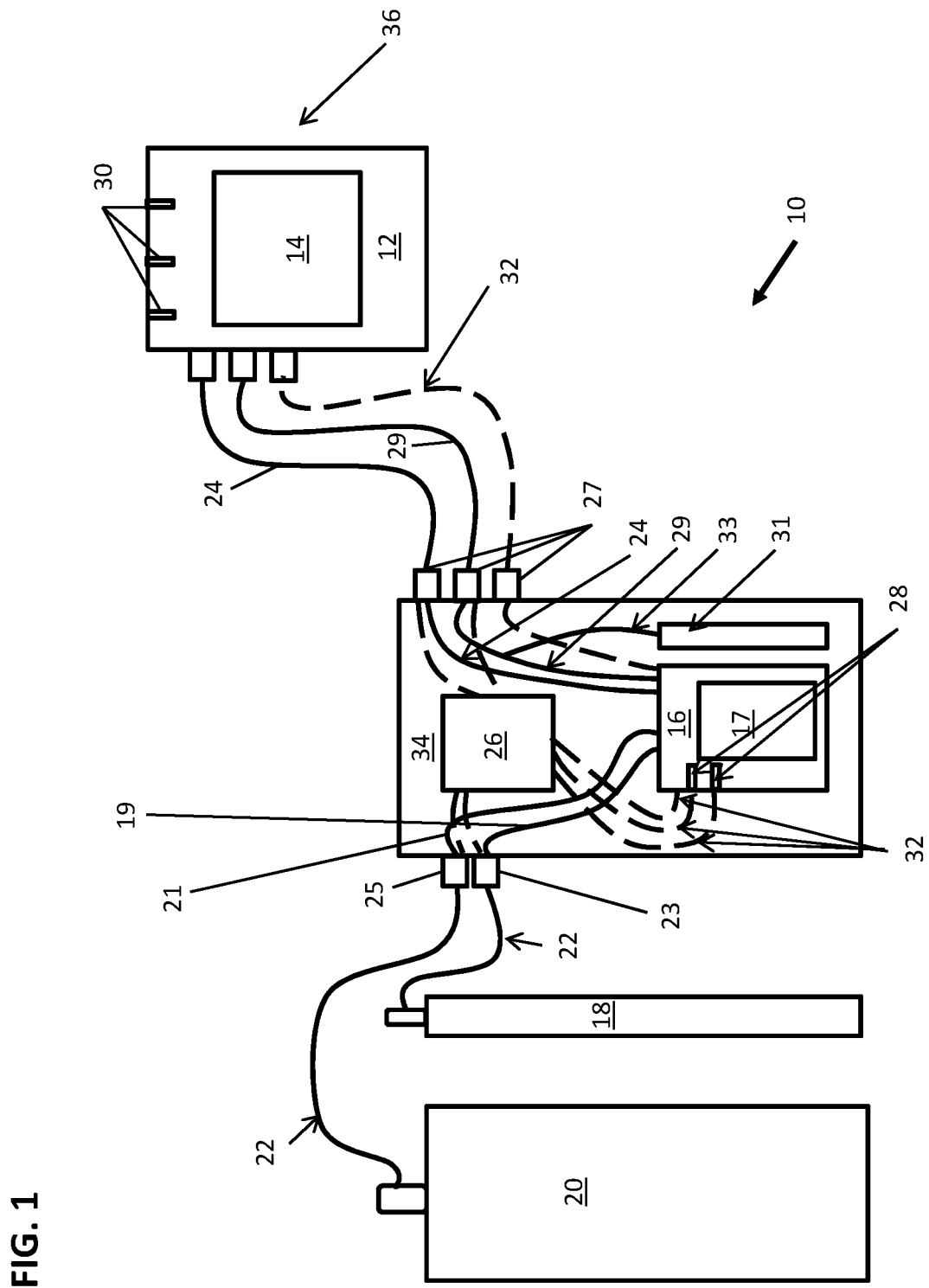
FIG. 1 shows a cryogenic device 10 including a cryoengine 16 connected to a cryogenic disinfection chamber 12, according to embodiments of the invention.

In one embodiment, shown in FIG. 1, a cryogenic device 10 including a cryogenic disinfection chamber 12 is provided. In use, an object 14, e.g., a package may be placed in the cryogenic disinfection chamber 12 for discrete, on-demand cryo-disinfection of the object 14. The object 14 may be described herein as, e.g., a package, but may be any other item to be disinfected such as, e.g., gowns, masks, personal protective equipment (PPE), instruments, and other goods.

The cryogenic disinfection chamber 12 is connected to a cryoengine 16, which provides the cryogen to cryogenic disinfection chamber 12. As used herein, the term cryoengine refers to a cryogenic system, cryogenerator, cryoconsole, cryogenic freezer, cryogenic cooling system, cryocooler, low temperature freezer, low temperature dewar, Joule Tompson cryogenic device, nitrogen-based cryogenic device, or any other device or system described in the art capable of generating and/or delivering a cryogenic fluid.

The cryoengine 16 draws a selected cryogen from one or more of an internal reservoir 17 or from an external reservoir. Where the reservoir is external, it may be, e.g., a cryogen gas cylinder 18 or a liquid cryogen cylinder 20 or both, as shown in FIG. 1. While FIG. 1 includes internal reservoir 17, cryogen gas cylinder 18, and liquid cryogen cylinder 20, it is expressly contemplated that embodiments according to the invention may include any one, any two, or all three of the cryogen sources depicted in FIG. 1.

Where the cryogen is drawn from the respective cylinder(s) 18, 20, the cryogen is delivered to the cryoengine 16 via cryogen hoses 22. In particular, gas cryogen is delivered to gas cryogen inbound port 23 and a gas cryogen inbound line 19, and/or liquid cryogen is delivered to liquid cryogen inbound port 25 and liquid cryogen inbound line 21, as appropriate to the configuration. The cryoengine 16 processes the cryogen into the appropriate state, e.g., gas, liquid, pressurized liquid, mixed gas and liquid phase, critical or supercritical state, and delivers the processed cryogen to the cryogenic disinfection chamber 12 via a supply line 24, which may pass through a connection port 27 as it leaves console 34 and as it enters cryogenic disinfection chamber 12, depending on the embodiment. After use in cryogenic disinfection chamber 12, used cryogen may be returned to cryoengine 16 via return line 29. Cryoengine 16 may also include a vent 31 and vent line 33. The cryogen used may be any one or more of nitrogen, argon, nitrous oxide, carbon dioxide, or other known cryogenic fluid. In some embodiments, the cryogen is nitrogen-based, offering the advantages of being readily available, relatively inexpensive, and inert, thereby providing a green solution. The cryoengine 16 may be of a type described in greater detail in any of U.S. Pat. Nos. 8,784,409; 9,974,592, 9,408,654, 10,054,262, US Patent Application Pub. No. US 2017/0172791 A1, or US Patent Application Pub. No. US 2018/0340654 A1, the contents of which are all incorporated by reference as though fully set forth herein.

A control system 26 is provided for monitoring system parameters, as detected or measured by sensors 28 in the cryoengine, as well as sensors 30 in the cryogenic disinfection chamber 12. The sensors 28, 30 are each coupled to the control system 26 by electrical and communications lines 32. Additionally, the control system 26 provides control of cryogen dispersal.

A number of arrangements for the control system 26, cryoengine 16, and cryogenic disinfection chamber 12 components are possible. In some embodiments, as shown in FIG. 1, the cryoengine 16 and control system 26 are contained within a console 34 which is housed separately from the cryogenic disinfection chamber 12 housing 36. In other embodiments, the cryoengine 16 and cryogenic disinfection chamber 12 may be integrated into a single housing, with the control system 26 within that same housing or located at a physically remote location. Or, in still further embodiments, the control system 26 may be located in a location physically remote from the cryoengine 16 housing and from the chamber housing 36. For example, the control system 26 may be located in a central control room within a facility where the device is being used, or the control system 26 may be mounted or integrated into the cryogenic disinfection chamber housing 36. In all of the various embodiments, the control system 26 is in communication with the cryoengine 16 and cryogenic disinfection chamber 12 via a wired or wireless communication device. Regardless of the arrangement with respect to the components' housing(s), the functions are carried out in the same manner.

Upon placing the object in the cryogenic disinfection chamber 12 and closing the chamber, cryogen is delivered from the cryoengine 16 to the cryogenic disinfection chamber 12. The cryogenic disinfection chamber 12 may contain a manifold or a series of cryogen manifolds (illustrated and discussed further in connection with manifolds 144 in the embodiment of FIG. 2) configured to deliver a spray or mist of cryogen to an interior of the cryogenic disinfection chamber 12. Each manifold (not shown in FIG. 1) may contain a single nozzle or multiple nozzles through which the cryogen passes, creating a mist-like spray within the cryogenic disinfection chamber 12. The nozzles vary in shape and in diameter, e.g., from about 0.0762 mm to 1.778 mm or larger, from about 0.1778 mm to about 1.5875 mm, or from about 0.4064 mm to about 0.9144 mm in diameter, depending on the cryogen employed. The cryogen manifolds and nozzles may be configured to deliver the cryogen spray into the chamber 12 or to deliver the cryogen spray to multiple surfaces of the object or package 14 within the chamber 12, e.g., top, bottom, and sides of the object or package 14. In such an embodiment, cryogen manifolds and/or nozzles may be located on a plurality of interior surfaces within the chamber 12, and may provide directional application of cryogen onto the plurality of surfaces of the object or package 14. In another embodiment, the cryogenic disinfection chamber 12 may include a manifold disposed on a moveable arm (not shown) that is configured to move, revolve, or rotate around the object 14, and/or change the angle of the manifold with respect to the object 14, to facilitate directional application of cryogen to various surfaces of the object 14. Regardless of the configuration or number of cryogen manifolds or nozzles, cryogen flow to each manifold can be independently controlled by valves or solenoids (not shown) positioned within the cryogenic disinfection chamber 12 or in the console 34, each of whose operation may be controlled by control system 26.

The misting of cryogen rapidly drops the temperature within the cryogenic disinfection chamber 12 from normothermic temperatures to, e.g., less than about −40° C., less than about −80° C., less than about −100° C., or less than about −140° C. These temperature changes may be accomplished in a period that may be, e.g., less than 5 minutes, or less than 1 minute. However, as is known in the art, the time to reach temperatures of, e.g., less than −40° C. varies depending on factors including, e.g., the size of the cryoengine 16 and cryogenic disinfection chamber 12. In one example, small objects 14 placed in a chamber 12 having a volume of about 48 cubic inches are lowered from normothermic temperatures to less than −140° C. in less than 10 minutes.

In another embodiment, the cryogenic disinfection chamber 12 may include a series of interconnected manifolds therein which do not contain nozzles. In such a configuration the interconnected manifolds create a cooling radiator matrix in which ultracold cryogen, e.g., nitrogen in liquid, pressurized liquid, mixed phase gas/liquid, critical, or supercritical form, is continually circulated, thereby creating an ultracold, e.g., −100° C. environment within cryogenic disinfection chamber 12 into which an object 14 is placed. Such an embodiment offers a less complex manifold design, but may decrease the processing speed, as exposure time to disinfect an object 14 will be longer than what is achievable with a spray manifold/nozzle configuration.

Once the cryogenic disinfection chamber 12 has reached a temperature of less than about −40° C., less than about −80° C., less than about −100° C., or less than about −140° C., the chamber 12 temperature can be maintained or further decreased for any desired length of time. Following the cryo-disinfection cycle, the cryogenic disinfection chamber 12 may be allowed to warm either passively or actively using a heating unit, e.g., a heated air circulator, an infrared heating array, a thermoelectric heater, a heat radiator, a reverse Joule Thompson heater using pressurized gas such as, e.g., helium, or other means as known in the art. Following warming, the object 14 may be removed from the chamber 12 or may be subjected to a subsequent cryo-disinfection cycle. This process may be repeated any number of times. The number of cryo-disinfection cycles and length of each cycle can vary from, e.g., 1 cycle to 10 cycles or more, with cycles ranging in duration from about one second to several minutes or longer.

Figure 2:
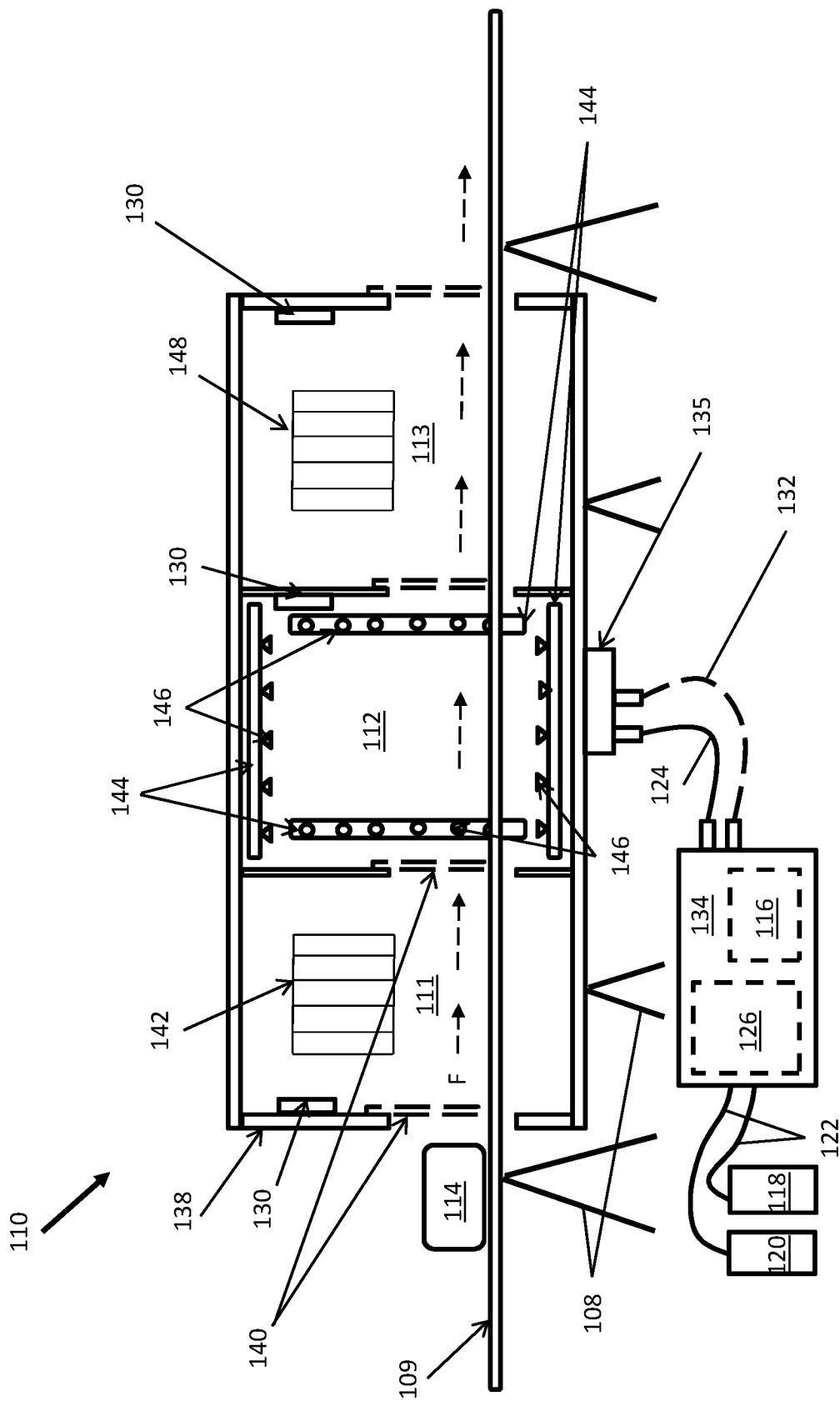
FIG. 2 shows a cryogenic disinfection tunnel device 110 including a cryoengine 16 connected to a plurality of chambers forming a tunnel, through which a conveyor belt carries an object to be disinfected, according to embodiments of the invention.

Turning next to FIG. 2, a cryogenic disinfection tunnel device 110 is illustrated and described herein. The cryogenic disinfection tunnel device 110 includes, in one embodiment, a multi chamber unit through which a conveyor belt 109 made of, e.g., mesh or solid material carries one or more objects 114 through various chambers including, e.g., a pre-cooling chamber 111, a disinfection chamber 112, and a post-cooling/warming chamber 113, in a flow direction F. In various embodiments, cryogenic disinfection tunnel device 110 including conveyor belt 109 may be supported by support legs 108. The cryogenic disinfection tunnel 110 provides rapid, hands-free continuous disinfection of objects conveyed there through, using a cryogen vortex spray tunnel. The objects 114 to be disinfected may be described herein as, e.g., packages, but may also be any other objects to be disinfected such as, e.g., gowns, masks, personal protective equipment (PPE), instruments, and other goods and items.

Like cryogenic device 10 of FIG. 1, cryogenic disinfection tunnel device 110 of FIG. 2 includes a cryoengine 116 which includes structures and functions analogous to cryoengine 16 described above with reference to FIG. 1. Cryoengine 116 draws a given cryogen from either an internal reservoir (not shown; analogous to internal reservoir 17 of FIG. 1) or an external reservoir such as, e.g., a cryogen gas cylinder 118 or a liquid cryogen cylinder 120 or both. The cryogen is drawn from the selected source and delivered to cryoengine 116 via cryogen hoses 122. Cryoengine 116 processes the cryogen into the appropriate state, e.g., gas, liquid, pressurized liquid, mixed gas and liquid phase, critical or supercritical state, and delivers the processed cryogen to the appropriate chamber in cryogenic disinfection tunnel 110 via a supply line 124. Cryoengine 116 may be of a type described in greater detail in any of U.S. Pat. Nos. 8,784,409; 9,974,592, 9,408,654, 10,054,262, US Patent Application Pub. No. US 2017/0172791 A1, or US Patent Application Pub. No. US 2018/0340654 A1, the contents of which are all incorporated by reference as though fully set forth herein. The particular cryogen used may be any one or more of nitrogen, argon, nitrous oxide, carbon dioxide or other known cryogenic fluid. In some embodiments, the cryogen is nitrogen-based, offering the advantages of being readily available, relatively inexpensive, and inert, thereby providing a green solution.

A control system 126 is provided for monitoring system parameters, as detected or measured by sensors in cryoengine 116 (not shown in FIG. 2, but analogous to sensors 28 in FIG. 1), as well as sensors 130, which may be arranged in arrays of sensors, and may be disposed within chambers 111, 112, and 113 of cryogenic disinfection tunnel 110. The sensors in cryoengine 116 and cryogenic disinfection tunnel 110 are each coupled to the control system 126 by electrical and communications lines 132 and electrical and communications interfaces 135 as necessary. Additionally, control system 126 may provide control of cryogen dispersal as well as other operational parameters such as, e.g., conveyor belt speed.

A number of arrangements are possible for the control system 126, cryoengine 116, and chambers 111, 112, 113 of cryogenic disinfection tunnel 110. In some embodiments, as shown in FIG. 2, the cryoengine 116 and control system 126 are contained within console 134, which is housed separately from the chambers 111, 112, 113 of cryogenic disinfection tunnel 110. In other embodiments, cryoengine 116 and chambers 111, 112, 113 of cryogenic disinfection tunnel 110 may be integrated into a single housing, with control system 126 within that same housing or located at a physically remote location. Or, in still further embodiments, control system 126 may be in a location physically remote from cryoengine 116 housing and from the cryogenic disinfection tunnel 110 housing. For example, control system 126 may be located in a central control room within a facility where cryogenic disinfection tunnel 110 is being used, or control system 126 may be mounted or integrated into a housing surrounding cryogenic disinfection tunnel 110. In all of the various embodiments, control system 126 is in communication with cryoengine 116 and cryogenic disinfection tunnel 110 via a wired or wireless communication device. Regardless of the arrangement with respect to the components' housing(s), the functions are carried out in the same manner.

In the embodiment illustrated in FIG. 2, three chambers 111, 112, 113 are provided, although more or fewer chambers may also be used in carrying out the present invention. In particular, as illustrated in FIG. 2, cryogenic disinfection tunnel 110 may include a pre-cooling chamber 111, a cryo-disinfection chamber 112, and a post-cooling chamber 113, through which an object 114 passes in series on the conveyor belt 109. In other embodiments, the cryogenic disinfection tunnel 110 may include a second pre-cooling chamber (not shown), a second disinfection chamber (not shown), and a second post-cooling chamber (not shown) downstream of the chambers 111, 112, 113 illustrated in FIG. 2. Such an embodiment results in the exposure of an object 114 to a plurality of cryo-disinfection cycles in a linear, continuous movement environment. Further additional chambers may also be provided to further increase the number of cryo-disinfection cycles. In another exemplary variation, a pre-cooling chamber 111 may be followed by a first disinfection chamber 112, then a second pre-cooling chamber (not shown, analogous to chamber 111), then a second disinfection chamber (not shown, analogous to chamber 112), followed by a post-cooling chamber (113). In yet another embodiment, merely a single disinfection chamber 112, or a single pre-cooling chamber 111 or a single post-cooling chamber 113 may be provided depending on the desired outcome.

As shown in FIG. 2, pre-cooling chamber 111 may include insulated walls 138 defining the bounds of the chamber 111, and a flexible wall portion 140 with an automatically reclose-able opening through which an object 114 may pass while carried in the direction of flow by conveyor belt 109. The flexible wall portion 140 may be disposed on each of an upstream side of pre-cooling chamber 111 along the conveyor belt 109, and a downstream side of the pre-cooling chamber 111 to facilitate ingress and egress of an object 114 carried by conveyor belt 109. The pre-cooling chamber 111 is cooled to a preset temperature, e.g., between ambient room temperature and about −80° C. Such cooling may be accomplished by a refrigeration unit 142 provided within or connected to chamber 111, or by a connection to cryoengine 116, wherein a specified amount of cryogen can be independently released into pre-cooling chamber 111 to achieve a desired chamber temperature. Like cryogenic disinfection chamber 12 of FIG. 1 and other chambers described herein, precooling chamber 111 includes sensors 130 including, e.g., sensors to measure temperature (e.g., thermocouple, thermistor, or infrared), pressure, and humidity; video, and other types of sensors known in the art for monitoring chamber parameters in real time, time lapse, or delay. The temperature of an object 114 (surface, internal, or both) may also be monitored independently or in conjunction with the chamber 111 temperature in real time, time lapse, or delay. The temperature of the cryogen may also be monitored within the cryoengine 116, chamber 111, cryotunnel 110, and/or cryogen flow path using any similar method.

Moving downstream along the flow path, an object moves from pre-cooling chamber 111 to disinfection chamber 112. As further shown in FIG. 2, the disinfection chamber(s) 112, analogous to cryogenic disinfection chamber 12 in FIG. 1, may contain a cryogen manifold 144 or a series of cryogen manifolds 144 configured to deliver a spray or mist of cryogen to an interior of disinfection chamber 112. Each manifold 144 may contain a single nozzle 146 or multiple nozzles 146 through which the cryogen passes, creating a mist-like spray within the chamber 112. The nozzles 146 vary in shape and in diameter, e.g., from about 0.0762 mm to 1.778 mm or larger, from about 0.1778 mm to about 1.5875 mm, or from about 0.4064 mm to about 0.9144 mm in diameter, depending on the cryogen employed. The cryogen manifolds 144 and nozzles 146 may be configured to deliver the cryogen spray into chamber 112 or to deliver the cryogen spray to multiple surfaces of the object 114 within chamber 112, e.g., top, bottom, and sides of the object 114. For example, cryogen manifolds 144 may be positioned such that nozzles 146 are directed upward from a bottom surface of the disinfection chamber 112, downward from a top surface of disinfection chamber 112, and inward from each of the side walls of disinfection chamber 112. Regardless of the configuration or number of cryogen manifolds 144 or nozzles 146, cryogen flow to each manifold 144 can be independently controlled by valves or solenoids (not shown) positioned within the disinfection chamber 112 or in the console 134, each of whose operation may be controlled by control system 126.

The misting of cryogen rapidly drops the temperature within the cryo-disinfection chamber 112 from normothermic temperatures to, e.g., less than about −40° C., less than about −80° C., less than about −100° C., or less than about −140° C. These temperature changes may be accomplished in a period that may be, e.g., less than 5 minutes, or less than 1 minute. As is known in the art, the time to reach temperatures of, e.g., less than −40° C. varies depending on factors including, e.g., the size of the cryoengine 116 and cryo-disinfection chamber 112.

In another embodiment, not illustrated herein, the cryo-disinfection chamber 112 may include a series of interconnected manifolds therein which do not contain nozzles. In this configuration, the interconnected manifolds create a cooling radiator matrix in which ultracold cryogen such as nitrogen, e.g., liquid, pressurized liquid, mixed phase gas/liquid, critical, or supercritical nitrogen, is continually circulated, thereby creating an ultracold environment having a temperature of, e.g., −100° C. within cryogenic disinfection chamber 112. Such an embodiment offers a less complex manifold design, but may decrease the processing speed, as exposure time to disinfect object 114 will be longer than what is achievable with a spray manifold 144 and nozzle 146 configuration such as the one illustrated in FIG. 2. Such embodiments may be combined with a pulsing or a slower moving conveyor belt 109.

After passing through the cryo-disinfection chamber 112, an object 114 may be carried by the conveyor belt 109 out of the cryo-disinfection chamber 112 and into a post-cooling chamber 113 through a flexible wall portion 140. The post-cooling or warming chamber 113 may be maintained at a preset temperature in the range of, e.g., about −80° C. to about +60° C. or greater by a heating unit 148 positioned within or connected to the chamber 113. The heating unit 148 may include circulated heated air, infrared heating, thermoelectric heaters, a heat radiator, reverse Joule Thompson heating using pressurized helium or other appropriate pressurized gas, or any other means of heating as known in the art. As described with respect to the other chambers, e.g., chambers 111, 112, the post-cooling chamber 113 may be monitored in real time, time lapse, or delay by any number of sensors 130 including, e.g., temperature, pressure, humidity, video, infrared, etc. Chamber 113 temperature can be monitored via thermocouple, thermistor, infrared, or any other means of measuring temperature. The temperature of an object 114 (surface, internal, both) within the chamber 113 may also be monitored independently or in conjunction with the chamber 113 temperature in real time, time lapse, or delay. After passing through the post-cooling chamber 113 on the conveyor belt 109, the object 114 may exit the chamber 113 via a flexible wall portion 140.

The speed of movement of the conveyor belt 109, as well whether such movement is continuous or pulsed, allows for control of the duration of exposure of an object 114 on the conveyor belt 109 to each chamber 111, 112, 113 described herein. Such motion control of the conveyor belt 109 may also allow a user to control the number of cycles to which an object 114 is exposed.

In use, as shown in FIG. 2, an object 114 is placed on the conveyor belt 109 outside and upstream of the pre-cooling chamber 111. The conveyor belt 109 carries the object 114 into the precooling chamber 111, where the object 114 is exposed to a temperature of, e.g., −10° C. to −80° C., or more particularly, −20° C., −40° C. or −80° C. The conveyor belt 109 then carries the object onward, through the flexible wall segment 140 between the pre-cooling chamber 111 and the cryo-disinfection chamber 112, and into the disinfection chamber 112. There, the object 114 is exposed to a spray mist of cryogen as described herein. In the disinfection chamber 112, the surface temperature of the object 114 is lowered to less than −40° C., e.g., less than −80° C. or less than −100° C. The conveyor belt 109 then moves the object 114 along through the cryogenic disinfection tunnel 110, and through the flexible wall portion 140 between the disinfection chamber 112 and the post-cooling chamber 113 into the post-cooling chamber 113. There, the object 114 warms to a temperature of, e.g., greater than −100° C. to +60° C. or greater and then emerges from the cryogenic disinfection tunnel 110.

As described above with reference to the cryogenic device 10 of FIG. 1 and the cryotunnel device 110 of FIG. 2, the length of time an object is exposed to the ultralow temperatures can vary depending on the desired depth of penetration into the object of the ultralow temperatures of, e.g., less than −40° C., less than −80° C. or less than −100° C. The desired temperature and depth of penetration may depend on the type of object to be disinfected and/or sterilized. For example, cryo-disinfection of textiles, e.g., articles of clothing, fabric masks, respirators, surgical scrubs, bedding, linens, curtains, etc., may be achieved by subjecting the textile materials to ultralow temperatures, e.g. of less than about −80° C., and maintaining exposure to such temperatures for, e.g., greater than one minute, for a plurality of minutes, or about 10 minutes in order to achieve complete penetration of the ultralow temperatures throughout the object.

The cryogenic device 10 of FIG. 1, or more particularly the cryotunnel device 110 of FIG. 2 may be used for cryo-disinfection of a cardboard box package 14, 114, and which may be sorted, processed, and/or delivered by a mail, express mail, or logistics entity, e.g., US Postal Service (USPS), United Parcel Service (UPS), Federal Express (FedEx), DHL International GmbH (DHL), or others worldwide. Cryo-disinfection of a cardboard box package 14, 114 may be achieved by subjecting the cardboard box to ultralow temperatures of, e.g., less than about −40° C., less than about −80° C., less than about −100° C., or less than about −140° C. for a period of, e.g., between about 1 second and about 60 seconds or about 120 seconds. The temperature and time period may be selected such that the ultralow temperature penetrates only to a depth of less than about 1 mm to about 1 cm or greater, or about 1 mm to about 5 mm. The duration of exposure necessary to achieve temperatures of, e.g., about −40° C. or less than about −80° C. at such depths may vary with the cryogen used and the material being disinfected, and shorter or longer exposure times, and single or multiple cycles of exposure are also possible. An exposure interval of 1 second up to 2 minutes using a nitrogen based cryogen, e.g., nitrogen gas, liquid, pressurized liquid, mixed phase gas and liquid, or critical or supercritical nitrogen, results in temperatures of less than −80° C. within this exposure time range in most non-insulated materials such as, e.g., cardboard, metal, plastic, masonry, ceramic, textiles, etc. In any event, such an embodiment may provide disinfection of the package 14, 114 or the outer surface of the container containing an item, without exposing the article(s) contained therein to the ultracold temperatures, thereby avoiding risk of damage to any items contained within the package. Longer exposure times result in deeper penetration of these ultralow temperatures as described above.

The use of a conveyor belt 109 in an embodiment similar to that of FIG. 2 increases throughput, which would facilitate its use in mail and distribution systems worldwide, in particular in central sorting facilities. As many as 1 million to 3 million objects or packages could be disinfected or sterilized daily in each tunnel, depending on its length. Such a system could also be used, albeit on a miniaturized scale, to disinfect instruments, objects, personal protective equipment, and other items, e.g., in a healthcare context.

In another embodiment applicable to either of cryogenic device 10 of FIG. 1, or to cryotunnel device 110 of FIG. 2, additional agents may be delivered to an interior of any of the chambers such as, e.g., cryogenic disinfection chamber 12 of FIG. 1, or chambers 111, 112, or 113 of FIG. 2. Additional agents may be delivered, e.g., through an additional manifold or manifolds and nozzle or set of nozzles within the particular chamber. The agents may include any agent capable of augmenting the pathogen destruction achieved by exposure to the cryogen. For example, the additional agent may be provided as a spray mist of hydrogen peroxide, isopropyl alcohol, hydroxy chloroquine, remdesivir, silver iodide, chlorine and chlorine compounds, formaldehyde, glutaraldehyde, ortho-phthalaldehyde, iodophors, peracetic acid, phenolics, and quaternary ammonium compounds, among other antibacterial agents, antiviral agents, and/or antifungal agents. In addition, any of the chambers described herein, including cryogenic disinfection chamber 12 in FIG. 1, or chambers 111, 112, 113 of FIG. 2 may include a fan therein to increase circulation within the chamber, and/or ultraviolet or infrared lighting to further add to the disinfection process.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cryogenic disinfection device comprising:
   a cryogenic disinfection chamber into which an object may be placed;
   a manifold disposed within the cryogenic disinfection chamber;
   a cryoengine configured to deliver a cryogen to the manifold, wherein the cryogen is a liquid phase cryogen, a gas phase cryogen, a pressurized liquid phase cryogen, a mixed gas and liquid phase cryogen, a critical fluid cryogen, or a supercritical fluid cryogen.

2. The cryogenic disinfection device of claim 1, wherein the manifold includes one or more nozzles configured to deliver a spray or mist of cryogen to an interior of the disinfection chamber.

3. The cryogenic disinfection device of claim 2, further comprising two or more manifolds, each manifold including one or more nozzles configured to deliver a spray or mist of cryogen to an interior of the disinfection chamber.

4. The cryogenic disinfection device of claim 3, wherein each of the one or more nozzles is independently controlled by a valve or solenoid.

5. The cryogenic disinfection device of claim 2, wherein the manifold is disposed on a movable arm, and is configured to be adjustably positioned within the disinfection chamber.

6. The cryogenic disinfection device of claim 1, wherein the manifold is one of a plurality of interconnected manifolds forming a cooling radiator matrix through which cryogen circulates.

7. The cryogenic disinfection device of claim 1, wherein the device is configured to achieve a desired temperature of −40° C., −80° C., −100° C., or −140° C. in less than 10 minutes.

8. The cryogenic disinfection device of claim 1, further comprising a heating unit configured to actively warm the disinfection chamber after completion of a cryo-disinfection cycle.

9. The cryogenic disinfection device of claim 8, wherein the heating unit is a heated air circulator, an infrared heating array, a thermoelectric heater, a heat radiator, or a reverse Joule Thompson heater using pressurized gas.

10. The cryogenic disinfection device of claim 1, further comprising a conveyor belt for carrying the object through the cryogenic disinfection chamber,
    wherein the cryogenic disinfection chamber includes a first flexible wall portion configured to allow ingress of the object carried by the conveyor belt, and a second flexible wall portion configured to allow egress of the object carried by the conveyor belt from the cryogenic disinfection chamber.

11. The cryogenic disinfection device of claim 10, wherein the conveyor belt comprises a mesh or a solid material.

12. The cryogenic disinfection device of claim 10, further comprising a pre-cooling chamber disposed adjacent to the cryogenic disinfection chamber,
    wherein conveyor belt is configured to carry the object through the pre-cooling chamber immediately prior to carrying the object through the cryogenic disinfection chamber.

13. The cryogenic disinfection device of claim 12, further comprising a refrigeration unit within the pre-cooling chamber, or a fluid connection from the cryoengine to the pre-cooling chamber, to cool the pre-cooling chamber to a temperature between ambient temperature and about −80° C.

14. The cryogenic disinfection device of claim 10, further comprising a post-cooling chamber disposed adjacent to the cryogenic disinfection chamber,
    wherein conveyor belt is configured to carry the object through the post-cooling chamber immediately after carrying the object through the cryogenic disinfection chamber.

15. The cryogenic disinfection device of claim 14, further comprising a heating unit disposed within or connected to the post-cooling chamber, the heating unit being configured to warm the post-cooling chamber to a temperature between about −80° C. and about +60° C.

16. The cryogenic disinfection device of claim 14, further comprising a second cryogenic disinfection chamber, disposed adjacent to the post-cooling chamber,
    wherein conveyor belt is configured to carry the object through the second cryogenic disinfection chamber immediately after carrying the object through the post-cooling chamber, thereby subjecting the object carried by the conveyor belt to a second cryogenic disinfection cycle.

17. The cryogenic disinfection device of claim 10, wherein the conveyor belt is configured for motion that is pulsed or continuous.

18. The cryogenic disinfection device of claim 1, wherein the cryogen is selected from the group consisting of: nitrogen, argon, nitrous oxide, and carbon dioxide.

19. The cryogenic disinfection device of claim 1, wherein the cryogen is nitrogen-based.

* * * * *